United States Patent [19]

Kovacevic

[11] Patent Number: 5,469,862
[45] Date of Patent: Nov. 28, 1995

[54] RANGE OF MOTION ANALYSIS SYSTEM

[75] Inventor: Nebojsa Kovacevic, Plymouth, Minn.

[73] Assignee: N.K. Biotechnical Engineering Company, Minneapolis, Minn.

[21] Appl. No.: 232,000

[22] Filed: Apr. 21, 1994

Related U.S. Application Data

[63] Continuation of Ser. No. 971,413, Nov. 19, 1992, abandoned.

[51] Int. Cl.⁶ .................................................. A61B 5/103
[52] U.S. Cl. ................................................ 128/782; 33/512
[58] Field of Search ................................ 128/774, 779,
128/782; 33/511, 512; 73/862.632, 862.629, 862.636, 862.637

[56] References Cited

U.S. PATENT DOCUMENTS

| | | | |
|---|---|---|---|
| 3,696,317 | 10/1972 | Farr | 73/862.632 |
| 4,037,480 | 7/1977 | Wagner | 128/782 |
| 4,062,355 | 12/1977 | Kaye | 128/779 |
| 4,267,725 | 5/1981 | Roth et al. | 73/862.65 |
| 4,323,080 | 4/1982 | Melhost | 128/774 |
| 4,436,099 | 3/1984 | Raftopoulos | 128/782 |
| 4,461,085 | 7/1984 | Dewar et al. | 33/512 |
| 4,534,364 | 8/1985 | Lamoreux | 128/774 |
| 4,649,934 | 3/1987 | Fraser et al. | 128/782 |
| 4,763,097 | 8/1988 | Kant et al. | 73/862.632 |
| 4,774,966 | 10/1988 | Lemmen | 128/774 |
| 4,804,000 | 2/1989 | Lamb et al. | 128/774 |
| 4,834,057 | 5/1989 | McLeod, Jr. | 128/782 |
| 5,050,618 | 9/1991 | Larsen | 128/774 |
| 5,158,096 | 10/1992 | Clark et al. | 128/777 |
| 5,163,228 | 4/1992 | Edwards et al. | 33/1 |
| 5,228,454 | 7/1993 | Siegler | 128/782 |

FOREIGN PATENT DOCUMENTS

| | | |
|---|---|---|
| 3443512 | 10/1985 | Germany . |
| 3634940 | 5/1987 | Germany . |
| 997674 | 6/1980 | U.S.S.R. . |
| 1306568 | 4/1987 | U.S.S.R. . |
| 9215248 | 9/1992 | WIPO . |

OTHER PUBLICATIONS

Gransberg et al, "A Computer Programmed System for the Analysis of Active and Passive Isokinetic Movements" Conference IEEE Frontiers of Engineering in Health Care in Washington, D.C. Sep. 1980, pp. 292–295.

Gere, James M. and Stephen Timoshenko, *Mechanics of Materials*, chapter 3, "Torsion", PWS Publishers, Boston, 1984, pp. 131–170.

"Automated Hand Functional Analysis" by B. P. Cahill, B. S. et al., from ISA, 1987 Paper #87–0106 pp. 35–38.

"Torque Range of Motion in the hand Clinic" by Donna Berger –Lee, MA, OTR, Judith Bell–Krotoski, OTR, FAOTA, and J. Wim Brandsma, PT, from the Journal of Hand Therapy, Jan.–Mar. 1990, pp. 7–13.

*Primary Examiner*—Stephen C. Pellegrino
*Assistant Examiner*—Guy V. Tucker
*Attorney, Agent, or Firm*—Westman, Chaplin & Kelly

[57] ABSTRACT

A system and method are disclosed for measuring range of motion of a body joint formed between a first body portion and a second body portion. The system includes a range of motion sensor comprising a support linkage having a first link joined to a second link for relative movement therebetween. The first link is adapted to be retained for movement with the first body portion and the second link is adapted to be retained for movement with the second body portion. An angular sensing device senses angular displacement of the second link relative to the first link and provides a representative indication thereof. A force sensing device joined to the support linkage senses the applied force to the first body portion and provides a representative indication thereof. Output signals from the angular sensing device and the force sensing device are provided to a signal processor for recording and analysis.

32 Claims, 6 Drawing Sheets

RANGE OF MOTION ANALYSIS SYSTEM

This is a continuation of application Ser. No. 07/971,413, filed Nov. 4, 1992, now abandoned.

BACKGROUND OF THE INVENTION

The present invention relates to an assembly for testing physical capabilities of a human test subject. More particularly, a machine and method are disclosed for measuring range of motion of to a body joint formed between two connected body portions.

A commonly measured physical capability is the range of motion of a particular body joint. The range of motion is the angular movement of one body portion to that of a second body portion from a reference position to a second position in a preselected path. Quantitative analysis of the range of motion is sometimes necessary in order to ascertain the extent of injury to the body joint. Other instances include the continued measurement of a person's capabilities during physical therapy.

Range of motion devices and systems to measure the range of motion of the body joint are commonly known. Generally, the device includes a first support structure connected to a first body portion of the body joint to be tested. A second support structure is connected to a second body portion forming the body joint. An angular measuring device connected between the first support structure and the second support structure measures the angular displacement of the second body portion relative to the first body portion. The angular measuring device determines the change in angular position between the first and second support structures, which corresponds to the angular change of position of the first body portion to the second body portion.

The range of motion of a body joint can be quantified as two separate motion components. The first motion component, commonly called "active" motion, is defined as the angular range the joint can be voluntarily articulated from the reference position in the preselected path. Whereas, the second component of motion, commonly called "passive" motion, is that remaining angular motion that an examiner can further cause by exerting some force on a body portion connected to the joint. Usually the amount of force that the examiner applies is determined by his or her experience and good judgment, or by complaints of pain from the patient. Although the passive motion tests are considered to be very important in defining the complete range of motion of the joint, the results obtained are questionable because the amount of force applied during the passive motion test is presently uncontrolled.

SUMMARY OF THE INVENTION

The present invention provides a system for measuring range of motion of a body joint formed between a first body portion and a second body portion. The system includes a range of motion sensor comprising a support linkage having a first link joined to a second link for relative angular movement therebetween. The first link is adapted to be retained for movement with the first body portion and the second link is adapted to be retained for movement with the second body portion. An angular sensing device senses angular displacement of the second link relative to the first link and provides a representative indication thereof. A force sensing device joined to the support linkage senses a force applied to the first body portion to induce pivotal movement relative to the second body portion and provides a representative indication thereof. Output signals from the angular sensing device and the force sensing device are simultaneously provided to a signal processor for recording and analysis.

The present invention further comprises a method for measuring the range of motion of the body joint. The method includes providing an assembly as described above; applying a force to the first body portion; and measuring angular displacement of the first body portion relative to the second body portion with the force applied. In a preferred method of operation, the angular displacement of the first body portion relative to the second body can be taken when the applying force value equals a selected proportion of a threshold force value. In a second preferred method of operation, the patient is supplied with a switch. The angular displacement of the first body portion relative to the second body is then taken when the patient experiences pain due to the applied force.

DETAILED DESCRIPTION OF THE PREFERRED EMBODIMENTS

Figure 1:
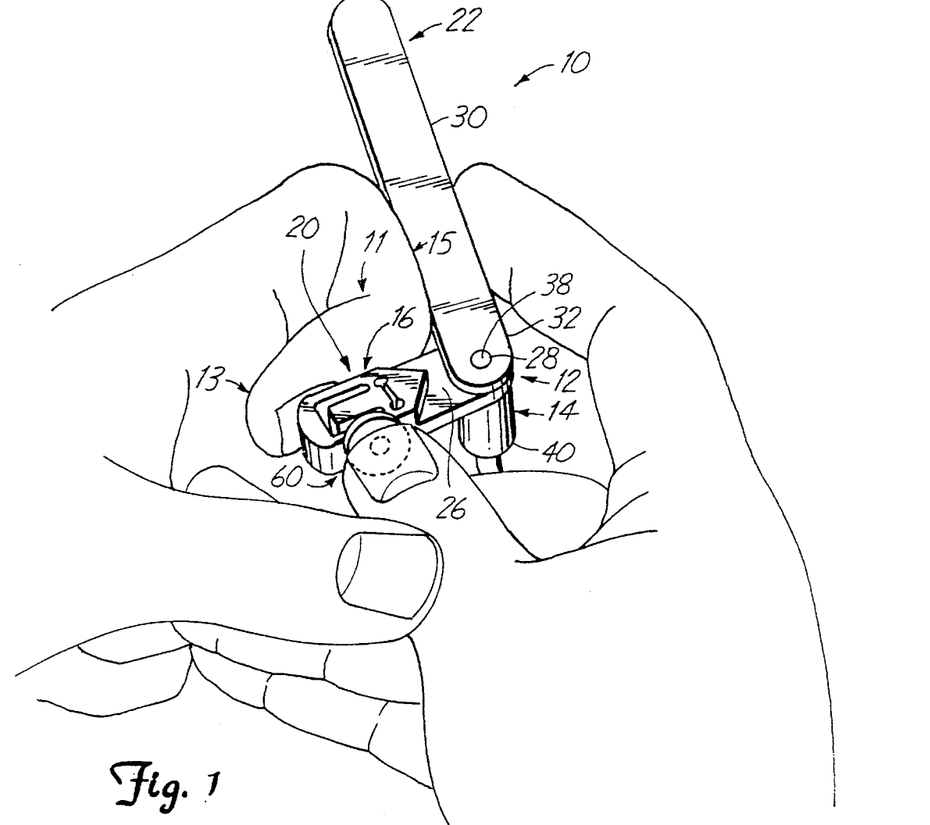
FIG. 1 is perspective view of a range of motion sensor for use in a range of motion analysis system of the present invention.

A range of motion sensor of the present invention is shown generally at 10 in FIG. 1 and is embodied as a finger joint tester. The sensor 10 includes a support linkage 12, an angular sensing device 14, and a force sensing device 16. When the sensor 10 is connected to a data acquisition unit 18 shown in FIG. 6, a range of motion analysis system 17 is formed. The system 17 provides quantitative measurement of a body joint, such as a knuckle, 11 connecting a first body portion 13 to a second body portion 15.

Figure 2:
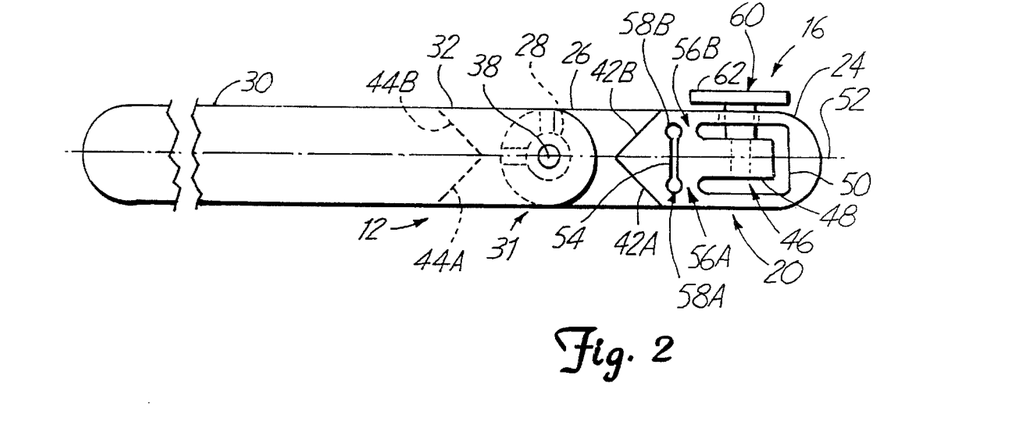
FIG. 2 is a top plan view of the sensor shown in FIG. 1 with parts broken away.
Figure 3:
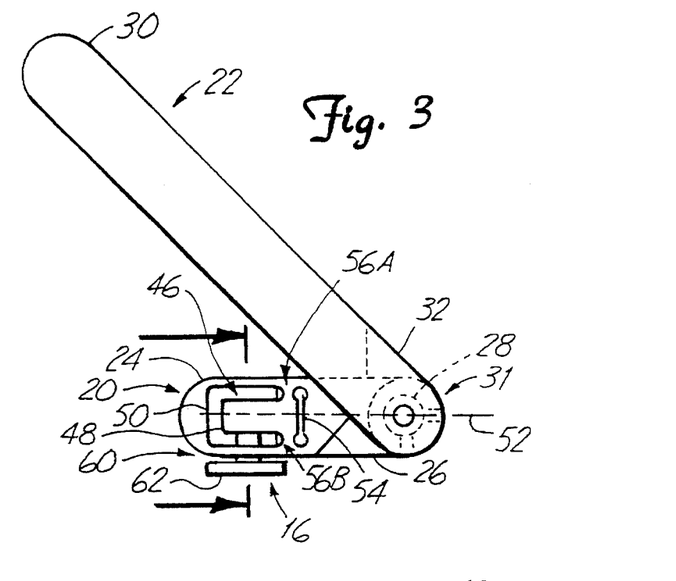
FIG. 3 is a top plan view of the sensor shown in FIG. 1.

The support linkage 12 of the sensor 10 includes a first link 20 joined to a second link 22. Referring also to FIGS. 2 and 3, the first link 20 comprises an extending portion 24 and a connecting portion 26. The connecting portion 26, as shown, is approximately one-half the thickness of the extending portion 24.

An aperture 28 is provided in the connecting portion 26 through which the first link 20 is connected to the second link 22. The second link 22 includes an extending portion 30 and a connecting portion 32 approximately one-half the thickness of the extending portion 30. When connected together to form the support linkage 12 having a pivotal connection 31, the thinner extending portion of the first link 20 overlaps the thinner extending portion of the second link 22 to provide a pivot assembly height approximately equal to that of the extending portions of either link.

The angular sensing device 14 senses the angular displacement between the second link 22 and the first link 20 about the pivotal connection 31. In the embodiment illustrated, the angular sensing device 14 comprises an electronic transducer in the form of a potentiometer having a first output terminal and a second output terminal. The potentiometer includes a center axial rod 38 connected to the first link 20, and a housing 40 connected to the second link 22. Rotation of the first link 20 relative to the second link 22 causes corresponding rotation of the rod 38 with respect to the housing 40. A conventional wiper, not shown, connected to one of the terminals is moved with respect to and in contact with a resistive element, not shown. As is conventionally known, the potentiometer provides a known resistance between the first output terminal and the second output terminal proportional to the rotational position of the center axial rod 38 with respect to the housing 40 from a reference position. Since the first link 20 and the second link 22 are secured to the center axial rod 38 and the housing 40, respectively, the resistance between the first output terminal and the second output terminal is in turn proportional to the angular relationship between the first link 20 and the second link 22, which is in turn proportional to the angular relationship between the first body portion 13 and the second body portion 15.

In the preferred embodiment, stop surfaces limit angular displacement of the first link 20 relative to the second link 22. Referring to FIG. 2 and the first link 20, the stop surfaces comprise walls or shoulders 42A and 42B where the connecting portion 26 forms the extending portion 24. These stop surfaces 42A and 42B are disposed approximately 90° with respect to each other, thereby allowing the second link 22 to pivot with respect to the first link 20 over an angular range of 270°. Similar stop surfaces 44A and 44B are formed on the second link 22 between the connecting portion 32 and the extending portion 30. The stop surfaces 42A, 42B, 44A and 44B prevent over-rotation of the potentiometer by limiting rotation of the center axial rod 38 with respect to the housing 40.

The force sensing device 16 senses the amount of torque applied to the first body portion 13 to induce pivotal motion relative to the second body portion 15. In the embodiment illustrated in FIGS. 1–4, the force sensing device 16 comprises a flexure member connected to free end of the first link 20. As illustrated in FIGS. 1–4, the flexure member comprises a beam 48 formed in the first link 20 by a U-shaped aperture 50. The beam 48 is substantially disposed on a longitudinal axis 52 of the first link 20. A slot 54 formed in the first link 20 substantially parallel to the lateral cross-width of the first link 20 forms parallel flexure straps 56A and 56B on opposite sides of the longitudinal axis 52. It should be noted that ends 58A and 58B of the slot 54 have generally circular apertures of diameter slightly larger than the width of the slot 54. The larger diameter ends 58A and 58B prevent localized stress concentration at the ends of the flexure straps 56A and 56B, which could lead to fatigue and eventual cracking.

Figure 4:
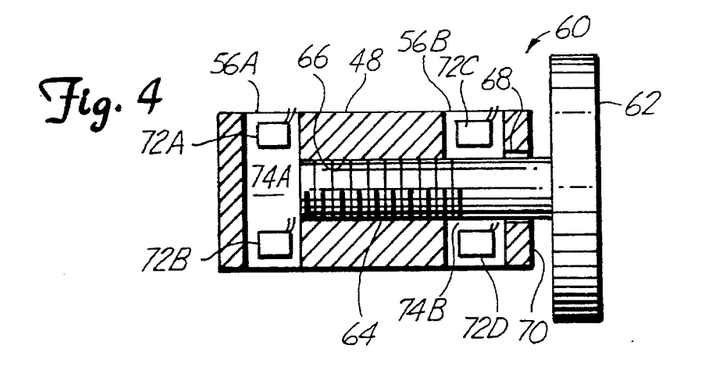
FIG. 4 is a sectional view taken as on line 4—4 in FIG. 3.

In order to measure "passive" motion, or involuntary articulation of the body joint 11, a force is applied to the body portion 13 by applying a force to the first link 20 while retaining the second link 22 in a substantially fixed position. In the embodiment illustrated in FIGS. 1–4, a force loading member 60 is attached to the beam 48 and comprises a push plate 62. Referring to FIG. 4, the push plate 62 is connected to a threaded shaft 64, which in turn is mounted in a suitable threaded aperture 66 in the beam 48. A through hole 68 is provided in a side wall 70 of the first link 20 such that the shaft 64 extends therethrough and the push plate 62 is spaced from the side wall 70.

Figure 5:
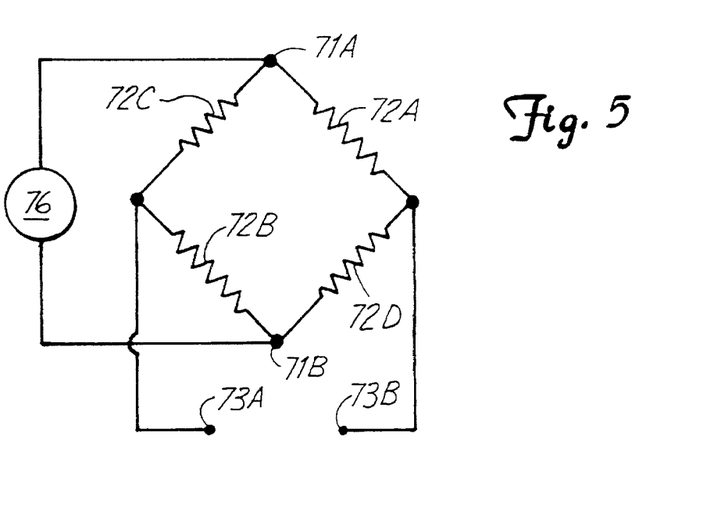
FIG. 5 is an electrical circuit schematically illustrating connection of strain gauges for use in the sensor of FIG. 1.

Four strain gauges 72A, 72B, 72C and 72D are conventionally adhered to inner surface 74A and 74B of the parallel flexure straps 56A and 56B, respectively, and provide a signal proportional to the applied force on the flexure member 46 and thus proportional to the applied moment on the body portion 13. As illustrated in FIG. 5, the strain gauges 72A–72D are connected in a conventional Wheatstone bridge with a suitable power source 76 connected to the strain gauges at terminals 71A and 71B. A representative output signal obtained across terminals 73A and 73B is proportional to the applied force. Connection of the strain gauges 72A–72D in a Wheatstone bridge circuit and properly mounting the strain gauges cancels torsion bending moments about the central longitudinal axis 52.

Figure 6:
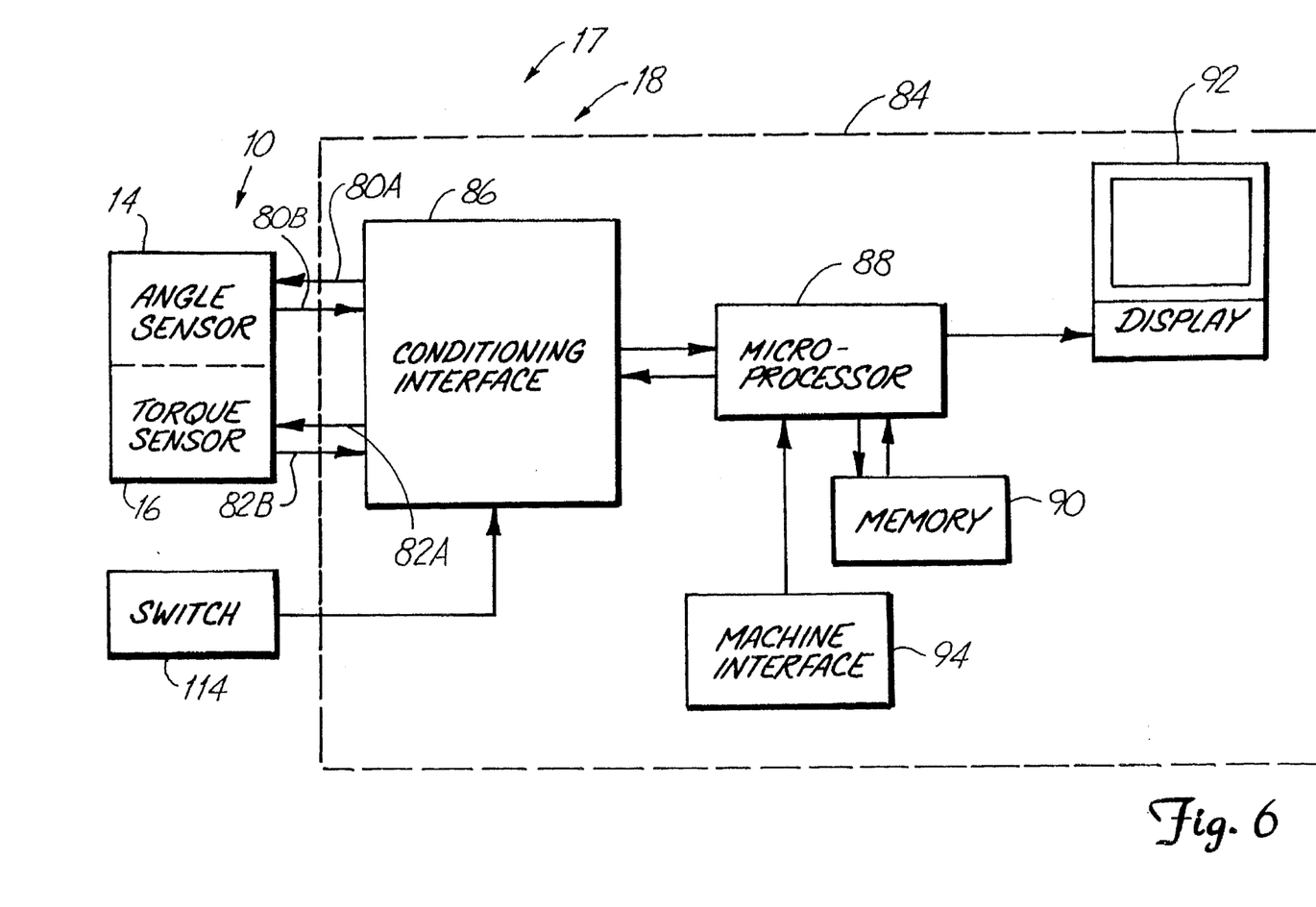
FIG. 6 is a block diagram representation of the range of motion analysis system.

The angular sensing device 14 and the force sensing device 16 are connected to the data acquisition unit 18 along signal lines 80A and 80B, and 82A and 82B, respectively, illustrated in FIG. 6. The signal processor 18 comprises a computer 84 having a conditioning interface 86 and a control processor 88, commonly known as a microprocessor. Memory 90 is connected to the microprocessor 88 for program and data storage. A visual display device 92 displays the relative values of the angular sensing device 14 and force sensing device 16 output signals, while a machine interface 94, preferably a keyboard, but which could be a function pad or the like, is connected to the microprocessor 88 for operator interaction.

Figure 7:
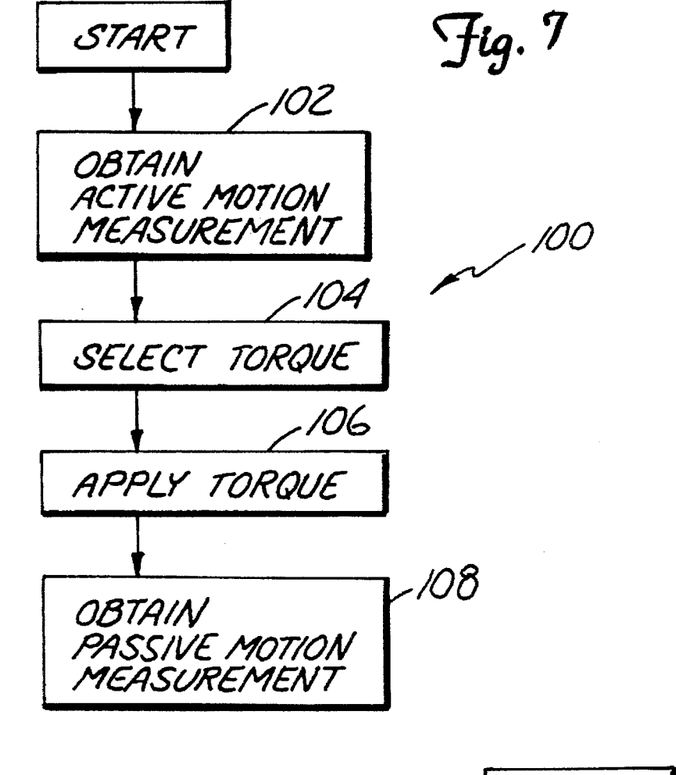
FIG. 7 and 8 are flow charts illustrating operation of the range of motion analysis system.

FIG. 7 illustrates operation of the system 10 according to a block diagram of a testing procedure 100, used to assess complete range of motion of the body joint 11. Specific individual steps of the testing procedure 100 are as follows:

Step 102: The patient is commanded to flex the body joint 11 completely. As illustrated in FIG. 1, the first link 20 is positioned adjacent the first body portion 13, while the second link 22 is rotated relative to the first link 20 to obtain a position adjacent the second body portion 15. The output signal from the angular displacement device 14, which is proportional to the angular displacement of the first body portion 13 relative to the second body portion 15, is converted and stored in memory 90. This measurement equals the active motion of the body joint 11.

Step 104: Using the interface device 94, the examiner preselects a desired force to apply to the first body portion 13 for determination of the passive motion.

Step 106: With the first link 20 substantially secured to the first body portion 13, the examiner applies a force to the push plate 62, which in turn is transferred through the support linkage 12 to create a moment on the body portion 13. It should be understood that the pivot connection 31 between the first link 20 and the second link 22 is substantially freely movable, offering little resistance to applied force. Thus, bending moments of the beam 48 relative to the parallel flexure strap 56A and 56B, substantially corresponds to the force applied to the first body portion 13. The force sensing device 16 provides an output signal proportional to the applied force, which is received by the computer 18 and compared with the preselected force value.

Step 108: When the applied force obtains a value proportional to the preselected force value, preferably equal to the force value, the output signal from the angular sensing device 16 is stored in memory 90. This measurement corresponds to the passive motion of the body joint 11. In the embodiment illustrated, the computer 84 provides an indicating signal, such as an audible tone, that represents that the preselected force value has been obtained, telling the examiner the applied force can be released.

The above-described testing sequence 100 is repeated until a sufficient amount of data is obtained. It should be understood that the order of measuring active motion and passive motion can be interchanged in that the active motion can be measured after measurement of passive motion. Individual active motion results and passive motion results can be statistically manipulated to obtain an average value or the like and displayed on the display device 92. Likewise, all results can be provided to a printer, plotter or similar recording device for future analysis.

Figure 8:
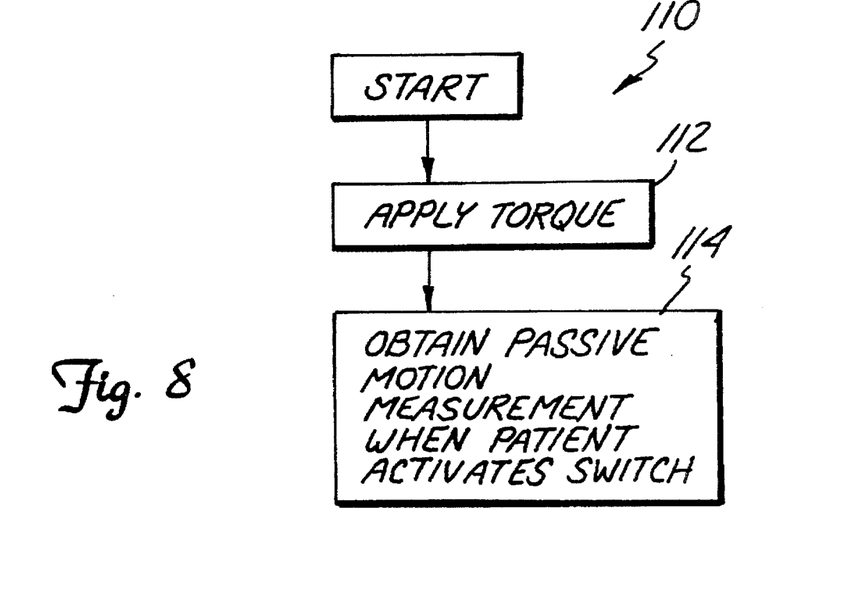

FIG. 8 illustrates in block diagram form operation of the system 17 according to a second testing procedure 110 shown in block diagram form and used to assess passive motion of the body joint 11. Specific individual steps of the testing procedure 110 are as follows:

Step 112: With the body joint 11 completely flexed and the support linkage 12 positioned as shown in FIG. 1 and described above, the examiner applies a force to the push plate 62, which in turn is transferred through the support linkage 12 to create a moment on the body portion 13.

Step 114: The patient operates a switch 114 connected to the computer 18, as illustrated in FIG. 6, when pain is perceived. Angular displacement of the body joint 11 and the applied force value are simultaneously recorded and stored in memory 90. The testing procedure 110 can be performed at regular intervals for a set time period, such as a month, to assess patient progress.

Figures 9, 10:
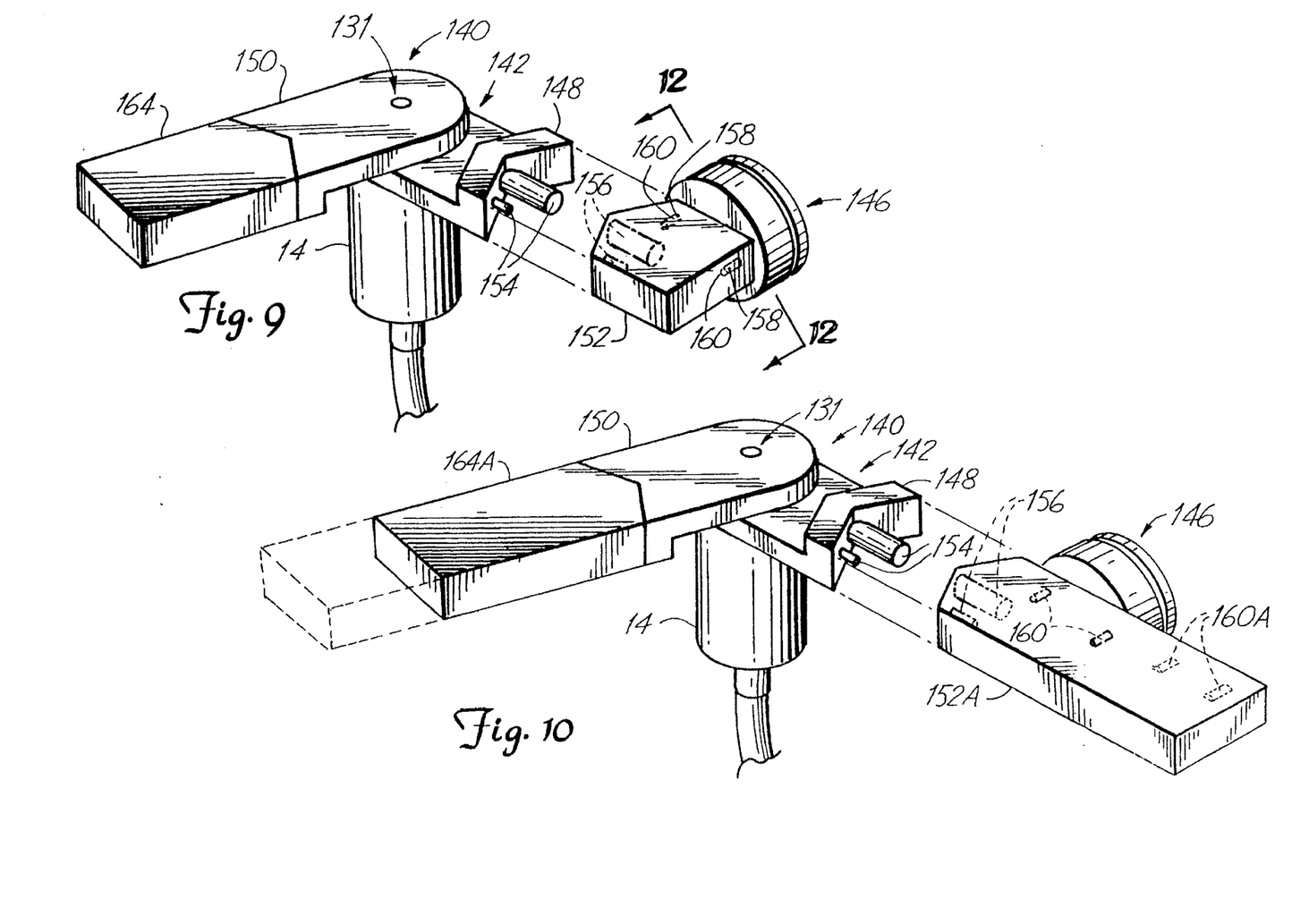
FIGS. 9 and 10 are perspective views of a second embodiment of a range of motion sensor.

A second preferred embodiment of the range of motion sensor of the present invention is shown generally at 140 in FIGS. 9 and 10. The sensor 140 includes a support linkage 142, having the angular sensing device 14, and a force sensing device 146, both of which sensing devices are connected to the data acquisition unit 18 shown in FIG. 6.

Like the support linkage 12 described above, the support linkage 142 includes a first link 148 pivotally joined to a second link 150. The angular sensing device 14 is mounted to the first link 148 and the second link 150 in the manner described above. Stop surfaces are disposed on at least one link approximately 90° with respect to each other to prevent over-rotation of the angular sensing device 14.

The force sensing device 146 senses the amount of force applied to the first body portion 13. A support member 152 connects the force sensing device 146 to the support linkage 142. Suitable mounting posts 154 provided on the support linkage 142 mount in corresponding apertures 156 provided in the support member 152. Additional mounting posts 158 and receiving apertures 160 join the force sensing device 146 to the support member 152. Preferably, the support member 152 can be removed and replaced with a support member 152A of a different length, as shown in FIG. 10. Since a force is applied through the force sensing device 146 in order to develop a moment on the body portion 13, radial displacement of the force sensing device 146 from the pivot connection 131 of the support linkage 142 further allows the examiner to control the amount of force applied. Alternatively, or in addition to selectively changing the length of the support member 152, additional mounting apertures 160A can be provided in the support member 152A to vary the distance of the force sensing device 146 from the pivot connection 131 to change the effective lever arm of the force sensing device from the pivot.

The second link includes a support member 164 mounted thereto using mounting posts similar to mounting posts 154. As shown in FIG. 10, the support member 164 can be removed and replaced with other support members 164A of longer longitudinal length when additional support is required.

Figure 11:
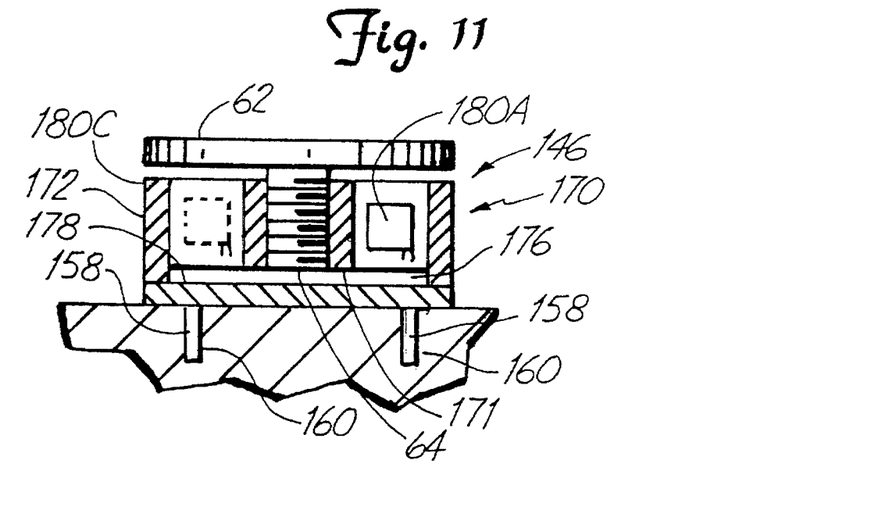
FIG. 11 is a sectional view of a force sensing device.
Figure 12:
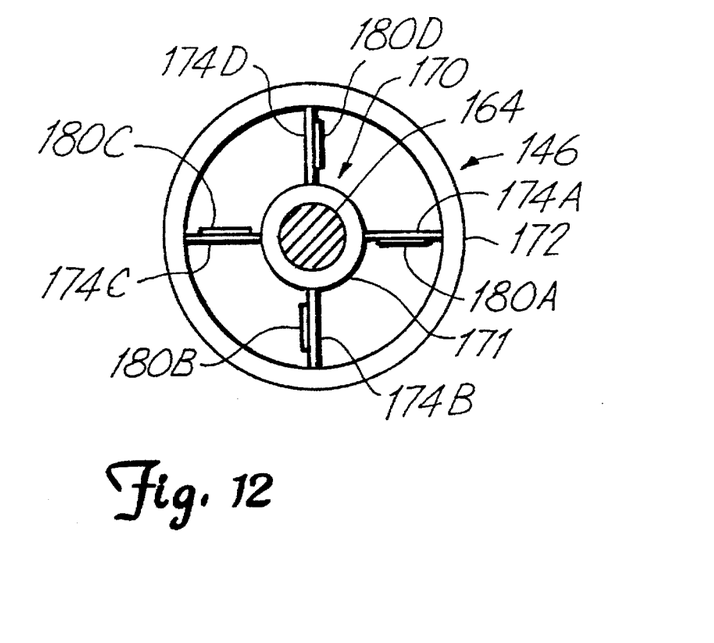
FIG. 12 is a sectional view of the force sensing device taken as on line 12—12 in FIG. 9.

The force sensing device 146 is shown in detail in FIGS. 11 and 12. As illustrated, the force sensing device 146 includes a flexure member 170 comprising an inner member 171. The inner member 171 is joined to a cylindrical support structure 172 with flexure walls 174A, 174B, 174C and 174D to provide a gap 176 between the inner member 171 and a lower portion 178 of the support structure 172. Force is applied to the push plate 62 which is connected to the inner member 171 with the threaded shaft 64. Although shown with four flexure walls angularly separated or radially displaced from each other by 90° it should be understood that any convenient number of flexure walls can be used. For example, in an alternative embodiment, three flexure walls can be used each separated from the other by 120° angular intervals. Preferably, the support structure 172, the inner member 171 and flexure walls 174A–174D are integrally attached to each other being formed from a single unitary piece.

Four strain gauges 180A, 180B, 180C and 180D are conventionally adhered to corresponding surfaces of flexure walls 174A–174D and provide a signal proportional to the applied force and thus the applied force. Like the strain gauges 72A–72D described above, the strain gauges 180A–180D are connected in a conventional Wheatstone bridge, similar to the circuit illustrated in FIG. 5, to cancel any torsion bending moments developed in the support member 152.

In summary, the present invention provides an assembly and method to test for range of motion of a body joint. The assembly measures both unassisted or active motion of the body joint as well as assisted passive motion. The passive motion of the body joint is referenced to a repeatable preselected-force applied to the first body portion, or alternatively, to pain experienced by the patient. Reference of the angular displacements of the body joint to an applied force insures that repeatable test sequences can be performed, thus obtaining accurate test data to compare changes in range of motion.

Although the present invention has been described with reference to preferred embodiments, workers skilled in the art will recognize that changes may be made in form and detail without departing from the spirit and scope of the invention.

What is claimed is:

1. A method for measuring angular displacement of a body joint formed from a first body portion connected to a second body portion, the method comprising:

providing a support linkage having a first link pivotally joined to a second link for relative angular displacement therebetween, the first link adapted to be retained for movement with the first body portion and the second link adapted to be retained for movement with the second body portion; angular sensing means joined to the support linkage for sensing angular displacement of the second link relative to the first link and providing a representative indication of angular displacement therebetween; force sensing means joined to the support linkage for sensing force applied to the first body portion to induce pivotal movement relative to the second body portion and providing a representative indication of the force applied; storing means for storing a selected representative indication of angular displacement, and for storing a selected representative indication of the force applied; and initiating means operated by the subject and connected to the storing means for initiating storing of the selected representative indication of angular displacement and for initiating storing of the selected representative indication of the force applied;

applying a force to the first body portion; and having the subject operate the initiating means to measure angular displacement of the first body portion relative to the second body portion with the force applied.

2. The method of claim 1 and further including an additional step of measuring angular displacement of the first body portion relative to the second body portion without the force applied.

3. The method of claim 1 and further including an additional step prior to the step of applying a force to the first body portion of storing a threshold force value and wherein the step of applying a force to the first body portion further comprises comparing a force value to the threshold force value, the force value corresponding to the applied force; and wherein the step of measuring comprises measuring the angular displacement of the first body portion relative to the second body portion when the applied force value equals a selected proportion of the threshold force value.

4. The method of claim 3 wherein the step of measuring comprises measuring the angular displacement of the first body portion relative to the second body portion when the force value equals the threshold force value.

5. An assembly for measuring angular displacement of a body joint formed between a first body portion and a connected second body portion of a subject, the apparatus comprising:

a support linkage comprising a first link pivotally joined to a second link for relative angular displacement therebetween about a pivot axis, the first link having a portion at a selected distance from the pivot axis to receive a force applied to the portion to develop a moment on the first body portion, the first link adapted to be retained for movement with the first body portion and the second link adapted to be retained for movement with the second body portion;

means for changing the selected distance of the portion from the pivot axis for adjusting the moment applied;

angular sensing means joined to the support linkage for sensing angular displacement of the second link relative to the first link and providing a representative indication of angular displacement therebetween;

force sensing means joined to the support linkage for sensing a force applied to the portion of the first link and providing a representative indication of the force applied; and storing means for storing a selected representative indication of angular displacement, and for storing a selected representative indication of the force applied.

6. The assembly of claim 5 wherein the force sensing means includes a flexure member joined to the first link.

7. The assembly of claim 6 wherein the force sensing means includes a strain sensor joined to the flexure member, the strain sensor providing the representative indication of the force applied as an electrical force output signal proportional to the applied force.

8. The assembly of claim 5 wherein the angular sensing means is an electronic transducer providing the representative indication of the angular displacement as an electrical angular output signal proportional to the angular displacement between the first and second links.

9. The assembly of claim 5 wherein the angular sensing means provides the representative indication of angular displacement as an electrical angular output signal proportional to the angular displacement between the first and second links, and the force sensing means provides the representative indication of the force applied as an electrical force output signal proportional to the applied force, and wherein the storing means comprises a signal processor for receiving the electrical angular output signal and the electrical force output signal.

10. The assembly of claim 9 wherein the signal processor includes display means for displaying an angular value proportional to the electrical angular output signal and a force value proportional to the electrical force output signal.

11. The assembly of claim 10 wherein the signal processor includes setting means for setting a threshold force value, and compare means for comparing the force value to the threshold force value, wherein the compare means initiates the storing means to store the angular value when the force value equals a selected proportion of the threshold force value.

12. The assembly of claim 11 wherein angular value is stored when the force value equals the threshold force value.

13. The assembly of claim 11 wherein the signal processor includes indication means for indicating when the force value equals a selected proportion of the threshold force value.

14. The assembly of claim 13 wherein the indication means indicates that the force value equals the threshold force value.

15. The assembly of claim 10 wherein the signal processor includes setting means for setting at least one threshold force value, and compare means for comparing the force value to a selected threshold force value, wherein the compare means initiates the storing means to store the angular value when the force value equals a selected proportion of one of the selected threshold force value.

16. The assembly of claim 5 further comprising initiating means operated by the subject and connected to the storing means for initiating storing of the selected representative indication of angular displacement and for initiating storing of the selected representative indication of the force applied.

17. The assembly of claim 5 wherein the force sensing means is joined to the first link.

18. The assembly of claim 5 wherein the force sensing means is replaceably joined to the first link.

19. The assembly of claim 5 wherein the means for changing the selected distance of the portion comprises a removable portion of the first link.

20. The assembly of claim 19 wherein the force sensing means is joined to the removable portion of the first link.

21. The assembly of claim 20 and further comprising means for adjusting a position of the force sensing means on the removable portion of the first link.

22. The assembly of claim 21 wherein the means for adjusting comprises a plurality of mounting apertures in the removable portion of the first link.

23. A kit for measuring angular displacement of a body joint formed between a first body portion and a connected second body portion of a subject, the kit comprising:

a linkage comprising a first linkage portion pivotally joined to a second linkage portion for relative angular displacement therebetween;

a plurality of support members of different lengths for individual attachment to the first linkage portion, wherein the first linkage portion and a selected support member attached thereto are adapted to be retained for movement with the first body portion and the second linkage portion is adapted to be retained for movement with the second body portion, and wherein the linkage and the selected support member are used to apply a moment on the first body portion by a force applied to the selected support member;

angular sensing means joined to the linkage for sensing angular displacement of the second linkage portion relative to the first linkage portion and providing a representative indication of angular displacement therebetween; and force sensing means joined to the linkage for sensing a force applied to the selected support member and providing a representative indication of the force applied.

24. The kit of claim 23 wherein the force sensing means is joined to the selected support member.

25. The kit of claim 24 wherein the force sensing means is replaceably joined to the selected support member.

26. The kit of claim 25 and further comprising a second plurality of support members of different lengths for individual attachment to the second linkage portion, wherein the second linkage portion and a selected support member from the second plurality of support members attached thereto are adapted to be retained for movement with the second body portion.

27. The kit of claim 23 and further comprising a mounting post for joining the selected support member to the first linkage portion.

28. The kit of claim 27 wherein the mounting post is joined to the first linkage portion and each of the support members includes an aperture for receiving the mounting post.

29. The kit of claim 28 wherein the first linkage portion has angled mounting surfaces, and wherein each of the support members has corresponding mounting surfaces adapted to mate with the angled mounting surfaces of the first linkage portion.

30. The kit of claim 29 wherein the mounting post is joined to the first linkage portion at an intersection of the angled mounting surfaces and wherein each of the support members includes an aperture for receiving the mounting post.

31. The kit of claim 27 and further comprising a second mounting post spaced apart from the first-mentioned mounting post.

32. The kit of claim 31 wherein the second mounting post is joined to the first linkage portion.

* * * * *

UNITED STATES PATENT AND TRADEMARK OFFICE
CERTIFICATE OF CORRECTION

PATENT NO. : 5,469,862
DATED : November 28, 1995
INVENTOR(S) : Nebojsa Kovacevic It is certified that error appears in the above-indentified patent and that said Letters Patent is hereby corrected as shown below:

Title page;

item [56] References Cited

U.S. PATENT DOCUMENTS

Reference No. 5 -- 4,323,080   4/1982
replace "Melhost" with --Melhart--.

Title page, OTHER PUBLICATIONS, Col. 2, line 10, replace "hand" with --Hand--.

Signed and Sealed this

Thirtieth Day of July, 1996

Attest:

BRUCE LEHMAN

*Attesting Officer*   *Commissioner of Patents and Trademarks*